United States Patent [19]
Goldberg

[11] 3,934,722
[45] Jan. 27, 1976

[54] STERILE NEEDLE PACKAGE
[75] Inventor: Allan M. Goldberg, Sepulveda, Calif.
[73] Assignee: American Hospital Supply Corporation, Evanston, Ill.
[22] Filed: Aug. 26, 1974
[21] Appl. No.: 500,292

[52] U.S. Cl. ............... 206/365; 215/232; 215/253; 215/305
[51] Int. Cl.² ......................................... B65D 85/24
[58] Field of Search ........................... 128/215–216, 128/218 R, 218 N, 218 NV; 206/363, 365–367, 370, 498; 215/304, 232, 253, 305; 220/284–286

[56] References Cited
UNITED STATES PATENTS

| | | | |
|---|---|---|---|
| 2,046,173 | 6/1936 | Lenhoff | 215/304 |
| 3,101,841 | 8/1963 | Baldwin | 206/365 |
| 3,149,717 | 9/1964 | Castelli | 206/365 |
| 3,333,682 | 8/1967 | Burke | 206/365 |
| 3,794,207 | 2/1974 | Hunt | 220/285 |

Primary Examiner—Donald F. Norton
Attorney, Agent, or Firm—Dawson, Tilton, Fallon & Lungmus

[57] ABSTRACT

A tamperproof sterile needle package including a relatively rigid cartridge loosely supporting a hypodermic needle for aseptic removal. After the cartridge is opened, the needle is removed by tipping the cartridge body and spilling the loosely-supported needle onto a sterile surface. When sealed within the cartridge, the needle and its tip are fully protected against damage and contamination despite the loose fit between the parts. The cartridge includes a cover with an integral lever which is lifted to pry the cover free of the body, without contaminating either the needle or the mouth of the cartridge, when removal of the needle is desired.

15 Claims, 6 Drawing Figures

U.S. Patent  Jan. 27, 1976  3,934,722
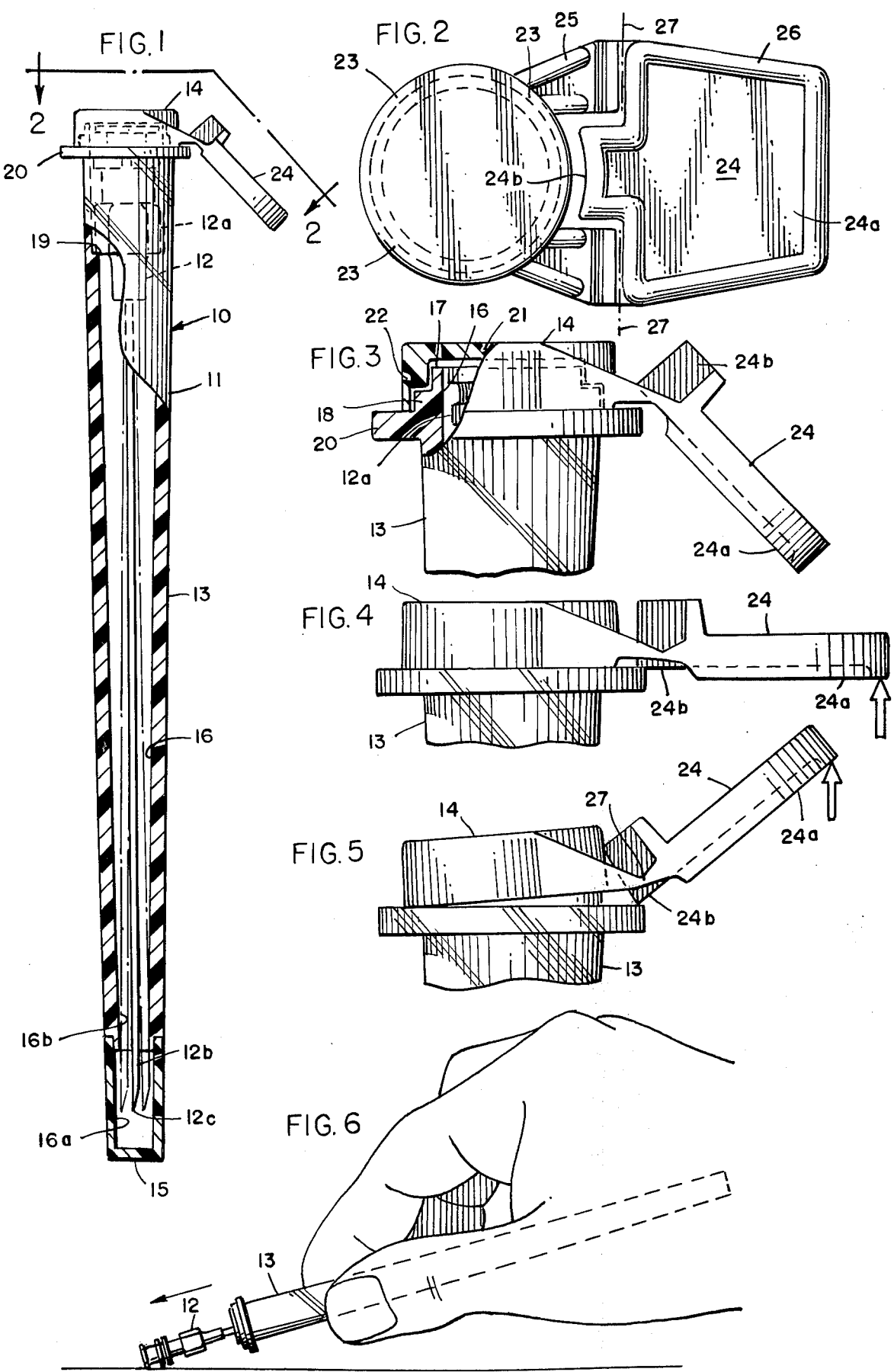

STERILE NEEDLE PACKAGE

BACKGROUND

Prior cartridges for storing sterile needles commonly include means for frictionally retaining the needles so that after the cartridges are opened the exposed hubs of the needles must be grasped to pull the needles from the cartridges. To avoid contamination of such a needle, or of the gloved hand used for extracting it, extreme care must be taken to make certain that the non-sterile surfaces of the cartridge cap do not contact the needle hub as the cartridge is opened, and that the sterile glove does not contact the non-sterile surfaces of the cartridge as the needle is grasped and removed. It is apparent that the consequences of inadvertently contaminating a spinal needle or other type of hypodermic needle during such removal could be extremely serious.

Loose packaging of needles in non-rigid or semi-rigid containers such as bubble packs is also known, but while such packs permit the needles to be spilled rather than pulled from their containers, they fail to insure avoidance of contamination problems. Thus, a danger exists that contaminating contact may inadvertently occur as the closure strip which seals the back of the bubble chamber is peeled away to expose the needle for removal.

Prior packages in which needles are loosely held also tend to present other serious problems. For example, the tip of a needle loosely supported in a flexible wrapper might engage the package wall and either puncture that wall or scrape material from it. In the latter event, even if the needle tip should remain free of particulate contamination, dulling or other damage to that tip might nevertheless occur.

References indicating the state of the prior art are U.S. Pat. Nos. 3,021,942, 3,101,841, 2,799,272, 2,854,976, 3,525,264, 3,149,717, 3,329,146, 3,333,682 and 3,370,588.

SUMMARY

One aspect of this invention lies in providing a needle package in which a hypodermic needle is loosely supported in a relatively rigid cartridge, and from which the needle may be easily "poured" or freely slid onto a sterile surface without danger that the needle might become contaminated during such a transfer. Because the needle hub does not project from the body of the cartridge to any appreciable extent, a user cannot grasp the hub and pull the needle from the cartridge; he must instead follow the proper aseptic technique of spilling the needle from the opened cartridge. Once the seal between the body and cover of the cartridge has been broken, the cover is incapable of being resecured to the body; hence, the cartridge is tamperproof for all practical purposes since prior rupture of the seal cannot be concealed.

Despite the fact that the needle is loosely held within the cartridge, there is virtually no danger of puncturing the cartridge wall, or of dulling, damaging, or contaminating the needle tip, partly because of the relatively rigid structure of the cartridge body and partly because the needle is suspended so that the tip is incapable of contacting the inside wall surface of the sealed cartridge.

The cover is readily separable from the cartridge body by means of a handle-equipped lever hingedly carried by the cover. Lifting of the handle serves the dual functions of prying the cover from the cartridge body and forcing the cover upwardly from the body's open end as the lifting action is continued. Since such action lifts the cover axially away from the body, there is virtually no danger that the mouth of the cartridge body might somehow become contaminated during the opening operation.

Briefly, the needle package comprises a cartridge having a stiff elongated tubular body closed at its lower end and open at its upper end. The open upper end is closed by a removal cover or cap, and a hypodermic needle, such as a spinal needle, is loosely supported within the sealed cartridge. Within the cartridge body is an annular ledge spaced downwardly from the body's upper end a distance approximating the length of the needle hub. The ledge supports the hub to suspend the needle with its sharpened tip spaced above the bottom of the cartridge body.

The body is also provided with an enlarged bottom chamber or compartment enclosing the tip, and with a relatively narrow neck portion communicating directly with the upper end of that compartment. The neck portion is engagable with the shaft of the needle directly above the needle tip to prevent the tip from engaging any portion of the inside surface of the enlarged bottom compartment.

Externally, the body is provided with an outwardly projecting annular shoulder spaced below the open upper end thereof. The cap is provided with a lower edge joined to that shoulder, and is also provided with a stiff lever hingedly connected to the cap along a hinge line extending in a plane substantially normal to the axis of the cartridge and spaced outwardly from that axis. The lever has a distal handle portion located outwardly beyond the hinge line and a proximal contact portion disposed inwardly from that line. As the handle is lifted from its normal lowered position into a raised position, the contact portion of the lever pivots downwardly into forceful engagement with the shoulder of the cartridge to pry the cap free from the body.

Other structural aspects of the invention, and the advantages and operation thereof, will become apparent from the specification and drawings.

DRAWINGS

FIG. 1 is a side elevational view, taken partly in section, showing a needle package embodying this invention.

FIG. 2 is an enlarged top plan view taken along line 2—2 of FIG. 1.

FIG. 3 is an enlarged fragmentary elevational view of the upper portion of the needle package, the structure being broken away to illustrate more clearly the relationship of parts.

FIG. 4 is an enlarged fragmentary elevational view illustrating an initial step in the opening of the package.

FIG. 5 is a fragmentary elevational view showing a further step in the opening of the package.

FIG. 6 illustrates the emptying of the cartridge by spilling the sterile needle onto a sterile supporting surface.

DETAILED DESCRIPTION

Referring to the drawings, the numeral 10 generally designates a needle package comprising a cartridge 11 and a needle 12. The needle is of the hypodermic type and, in the illustration given, is a spinal needle; however, it will be understood that other types of needles may be supported within the cartridge. The upper end of the needle is provided with an enlarged hub 12a for attachment to a suitable syringe. At its lower end, the needle terminates in a tip portion 12b with sharpened bevel edges 12c. Since the construction of such a needle is entirely conventional and well known, further description is believed unnecessary herein.

Cartridge 11 includes a body 13 and cap 14. As shown in FIG. 1, the body is elongated and tapers towards its closed lower end 15. The tubular body defines a chamber 16 and is open at its upper end for removal of the needle stored therein. It will be observed from FIGS. 1 and 3 that there is an annular spacing between the outside surface of hub 12a and the surface of chamber 16 or, in other words, that the needle is loosely received within the chamber of the cartridge. It will also be observed that the upper end of the hub is at approximately the same level as the top 17 of the cartridge body. The top of the needle hub need not be at precisely the same level as the upper end of the cartridge body and in some cases it may be desirable to extend the collar portion 18 a substantial distance above the hub. It is important, however, that the open upper end of the hub not extend any substantial distance above the top surface 17 of the cartridge body so that a user cannot empty the cartridge by grasping the needle and withdrawing it from the cartridge body.

The needle is supported in chamber 16 by annular ledge 19. The enlarged portion of hub 12a rests upon the ledge to suspend the needle with its tip 12b spaced well above the bottom 15 of the cartridge. Tip portion 12b is disposed within an enlarged chamber portion or compartment 16a. The cross sectional dimensions of compartment 16a are substantially greater than the neck portion 16b of the chamber directly thereabove. The walls of neck portion 16b are engagable with the shaft of hollow needle 12 directly above tip portion 12b to prevent the tip from engaging any surface within compartment 16a. The range of lateral movement of the tip portion is illustrated in broken lines in FIG. 1. While the needle is only loosely held, and is capable of considerable lateral movement within the cartridge, the tip with its sharpened edges is protected against contact with the cartridge that might dull the edges, deform or otherwise damage the tip, or cause a scraping action that could contaminate the tip and the lumen of the needle with particulate material.

In the illustration given, the portion of the cartridge body defining compartment 16a is formed separately and is then cemented or otherwise secured to the remainder of the cartridge body directly thereabove; however, it is to be understood that such a construction is primarily one of manufacturing convenience and that if desired the entire body may be formed as an integral unit.

Referring to FIGS. 1 and 3, an annular shoulder 20 projects outwardly from the cartridge body directly below collar 18. Cap 14 has a top wall 21 and an integral depending side wall 22, the bottom surface of the side wall engaging the top of shoulder 20 and being heat welded or otherwise secured thereto at a plurality of circumferentially spaced points 23 (FIG. 2). If desired, the outer surface of collar 18 and the opposing surface of side wall 22 may be stepped as shown in FIG. 3 to redeuce the thickness of wall 22 at its lower limits, thereby reducing the strength of the attachment between the cap and cartridge body. As clearly depicted in FIG. 3, there is an appreciable space between the outer surface of collar 18 of the cartridge body and the inside surface of the cap's side wall 22, with the result that firm attachment between the cap and cartridge body is achieved only because of the fusion or other means used to secure the v⁻ 'ersurface of side wall 22 to shoulder 20. Once the points of connection between the parts are broken, cap 22 is incapable of being securely fitted upon the collar.

Rupturing of the points of attachment between the cap 14 and the cartridge body 13, and removal of the cover, is achieved by manipulation of lever 24. The lever 24 is formed integrally with the cap, being a continuation of a pair of spaced arms or projections 25 extending outwardly from a side portion of the cap. The lever includes an enlarged handle portion 24a and a reduced contact or lug portion 24b. The lever is relatively rigid, being reinforced by beading 26, but it connects or merges with the remainder of the cap along a thin web of material defining a hinge line 27 extending in a plane normal to the longitudinal axis of the cartridge and spaced outwardly a substantial distance from that axis. It will be noted from FIGS. 2–5 that the length of the handle portion 24, measured outwardly from hinge line 27, is substantially greater than the length of lug porion 24b measured from that same hinge line.

Normally the lever assumes the downwardly inclined or lowered position illustrated in FIGS. 1 and 3. It may, however, be pivotted into the raised positions of FIGS. 4 and 5 and, when so raised, the free end of lug portion 24 swings into contact with the upper surface of shoulder 20 (FIG. 4). Continued lifting of handle portion 24a causes rupturing of the bonds of attachment between the cover and cartridge body with such lifting movement ultimately resulting in complete removal of the cap from the body. Since such removal is achieved by uninterrupted upward movement of the handle portion 24a, the possibilities that non-sterile external surface portions of the cap might somehow be brought into contact with collar 18 or needle 12 are virtually non-existent. Both the internal and external surface of the collar remain sterile and, therefore, the needle may be easily slipped or poured from the cartridge body onto a suitable sterile surface without danger of needle contamination.

Referring particularly to FIG. 5, it will be seen that lug portion 24b also projects upwardly a substantial distance above hinge line 27 and is engagable with the side wall of the cap to limit further upward pivotal movement of lever 24 about that hinge line. The lug portion therefore locks the lever against further upward pivotal movement relative to the cap, so that continued upward force exerted upon the handle portion of the lever is transmitted directly to the cap to facilitate lifting of the cap from the cartridge body.

The cap and cartridge body are preferably formed of plastic although other materials such as metal might conceivably be used. Polypropylene has been found particularly effective although other plastics having similar properties may be used.

While in the foregoing an embodiment of the invention has been disclosed in considerable detail for purposes of illustration, it will be understood by those skilled in the art that many of these details may be varied without departing from the spirit and scope of the invention.

I claim:

1. A needle package comprising a cartridge having a stiff elongated tubular body closed at its lower end and open at its upper end, a removable cap closing said open upper end, and a needle loosely supported within said cartridge, said needle having a sharpened tip portion at its lower end and an enlarged hub at its upper end, said cartridge body being provided with an internal ledge spaced below the body's upper end and engaging the underside of said hub to support said needle with the tip portion thereof spaced from the bottom of said body, said body also being provided with an enlarged compartment enclosing said tip portion and a relatively narrow neck portion directly above said compartment, said neck portion being engagable with said needle above said tip portion to prevent said tip portion from engaging the inside surface of said compament.

2. The needle package of claim 1 in which said internal ledge is spaced below the body's upper end a distance no less than the approximate axial length of said hub.

3. The needle package of claim 1 in which said cartridge body is provided with an outwardly projecting annular shoulder spaced below the open upper end thereof, said cap having a lower edge joined to said shoulder.

4. The needle package of claim 3 in which said cap is also provided with a lever hingedly connected to said cap along a hinge line extending in a plane substantially normal to the axis of said cartridge and spaced outwardly from said axis, said lever having a handle portion disposed outwardly beyond said hinge line and movable between a lowered position nd a raised position, said lever also having a lug portion disposed inwardly of said hinge line and movable downwardly into engagement with said shoulder, as said handle portion is raised, to pry said cap free from said body.

5. The needle package of claim 4 in which said handle portion has a length substantially greater than said lug portion as measured from said hinge line.

6. The needle package of claim 4 in which said lug portion also projects upwardly above said hinge line, said lug portion above said hinge line being engagable with said cap to limit upward movement of said lever about said line and to cause a lifting of said cap from said body as continued upward force is exerted upon said handle portion.

7. The needle package of claim 1 in which said cartridge body and said cap are formed from relatively rigid plastic material.

8. A needle package comprising a cartridge having a tubular body open at its upper end and adapted to support a sterile needle therein, said body having an annular shoulder spaced below the open upper end thereof and projecting outwardly from said body, and a cap fitting over the open upper end of said body and having a lower edge joined to said shoulder, said cap being provided with a lever hingedly connected thereto along a line extending in a plane substantially normal to the axis of said cartridge and spaced outwardly from said axis, said lever having a handle portion disposed outwardly beyond said hinge line and movable between a lowered position and a raised position, said lever also having a lug portion disposed inwardly of said hinge line and movable downwardly into engagement with said shoulder to pry said cap free from said body when said handle portion is raised.

9. The needle package of claim 8 in which said cap is fused to said body at a plurality of points spaced circumferentially about said shoulder.

10. The needle package of claim 8 in which said handle portion has a length substantially greater than said lug portion as measured from said hinge line.

11. The needle package of claim 8 in which said cap has top and side walls, said lug portion of said lever also projecting upwardly above said hinge line for engagement with the side wall of said cap when said lever is in its raised position, thereby limiting further upward movement of the handle portion of said lever about said hinge line.

12. The needle package of claim 8 in which said cap and cartridge body are formed of relatively rigid plastic material.

13. The needle package of claim 8 in which a hub-equipped needle is loosely supported within said tubular body.

14. The needle package of claim 13 in which said cartridge body is provided with a bottom wall spaced below the tip of said needle, and means disposed within said cartridge body above the tip of said needle for preventing contact between said tip and the interior of the tubular body.

15. The needle package of claim 13 in which said needle includes a hub portion supported within said body adjacent the open upper end thereof, said hub havng its upper limits at substantially the same level as the upper opening of the cartridge body.

* * * * *